United States Patent [19]

Finner et al.

[11] 4,422,319

[45] Dec. 27, 1983

[54] APPARATUS FOR TESTING GRAINS FOR RESISTANCE TO DAMAGE

[75] Inventors: Marshall F. Finner, Middleton; Shiw S. Singh, Madison, both of Wis.

[73] Assignee: Wisconsin Alumni Research Foundation, Madison, Wis.

[21] Appl. No.: 303,966

[22] Filed: Sep. 21, 1981

[51] Int. Cl.³ .............................................. G01N 3/30
[52] U.S. Cl. ....................................................... 73/12
[58] Field of Search ...................... 73/11, 12; 324/173, 324/174

[56] References Cited

U.S. PATENT DOCUMENTS

| | | | |
|---|---|---|---|
| 2,585,657 | 2/1952 | Keefer | 73/12 |
| 2,976,717 | 3/1961 | Davoust | 73/12 |
| 3,676,765 | 7/1972 | Westcott | 324/174 |

OTHER PUBLICATIONS

"A Mechanical Damage Susceptibility Tester for Shelled Corn," Ramesh Sharda and Floyd L. Herum, American Society of Agricultural Engineers, 1977 Winter Meeting.

"A Centrifugal Gun for Impaction Testing of Seeds," J. Robert Cooke and James W. Dickens, 1971 Transactions of the ASAE, pp. 144-155.

Primary Examiner—S. Clement Swisher
Attorney, Agent, or Firm—Isaksen, Lathrop, Esch, Hart & Clark

[57] ABSTRACT

Corns and other grains are tested for resistance to breakage during shipment by being fed to a rapidly rotating impeller (30) mounted within a cylindrical impact chamber (16). The grains are metered into the center of the impeller (30) by a metering device (12) at a controlled rate, and are thereafter spun outward through channels formed within the solid impeller disk (60) to strike the smooth surfaced inner wall (35) of the impact chamber (16) at consistent velocities. The smashed grains fall through a collection chute (17) into a box (20) and are subsequently screened to determine the relative percentage of broken and unbroken grains. The rate of speed of the impeller (30) and the metering device (12) are controlled to insure uniformity of testing between each sample.

14 Claims, 5 Drawing Figures

APPARATUS FOR TESTING GRAINS FOR RESISTANCE TO DAMAGE

TECHNICAL FIELD

This invention pertains generally to the field of agricultural equipment and particularly to devices for testing grains such as corn to determine the resistance of the grain to damage during handling.

BACKGROUND ART

The shipment of food grains over long distances has become commonplace in the modern world, with a substantial trade activity taking place both across the country and overseas. Grains, such as corn, wheat, oats, soybeans, etc., are often handled many times during the shipment and storage process before they find their way to the ultimate consumer. The repeated handling of the grains during shipment and storage results in physical abrasion of the shells of the grain, with a significant percentage of the individual grains having their shells broken open. Such damage to the protective outer shell of the grain enhances the probability that the grain will be spoiled, moldy, or otherwise contaminated by the time it reaches the consumer.

Corn and other grains are graded at the time that they are first brought to market on several qualities including weight/density, moisture percentage, apparent mold growth or other damage, and proportion of grain having broken shells. For example, corn is regularly tested and graded to determine the amount of "broken corn and foreign material" (BCFM) contained in the corn, and the percentage found in such screening processes determines the grade of the corn; e.g., a two percent increase in the proportion of broken corn may reduce the corn grade from No. 1 corn to No. 3 corn. Naturally, the higher grade corn demands a higher price in the marketplace.

While the grade of the corn may be known by the purchaser at the time the purchase is made, if the corn is thereafter to be transported long distances, such as overseas, the handling and jostling that the grain takes during shipment may result in substantial breakage of the individual grains. As a result, the grain at the point of use may be of a substantially lower grade than it was at the point at which it was purchased.

It is known that not all varities of grain have the same resistance to breakage during handling. Thus, it is very desirable to be able to predict whether the particular grain being purchased is more or less susceptible to breakage during the handling process. A commercial breakage tester, manufactured by Fred Stein Laboratories, Inc., of Atchison, Kansas, has been used commercially to test the mechanical strength of corn and other grain. This tester agitates grains held in a stainless steel cup by a rotating blade. Rotary or centrifugal guns for impact testing of grains are also known although not presently used commercially. See "A Mechanical Damage Susceptibility Tester for Shelled Corn," Ramesh Sharda and Floyd L. Herum, American Society of Agricultural Engineers, 1977 Winter Meeting; "A Centrifugal Gun for Impaction Testing of Seeds," J. Robert Cooke and James W. Dickens, 1971 Transaction of the ASAE, pp. 147-155. The high cost of commercial testers and the amount of time required to test a batch of grain has hindered wide spread use of the testers. Difficulties have been encountered with both commercial and proposed grain breakage testers in obtaining repeatability of the test results for samples of grain taken from the same batch or load. The failure of a tester to yield repeatable results reduces the confidence in the tester's ability to predict a likely level of damage in a grain after it has been shipped. The difficulty of testing the grains for breakage reliably becomes particularly acute for very durable grains which may show very little breakage when subjected to conventional testing methods. However, under the stress of repeated handlings that occur in overseas shipment, a significant percentage of even such durable corn has been observed to break and deteriorate; and it has also been observed that different varieties or batches of the more durable kinds of corn show different levels of resistance to breakage during long distance shipment. Up to now, it has not been possible to reliably descriminate between the more durable varieties of corn in order to predict their expected damage levels resulting from long distance shipment.

DISCLOSURE OF THE INVENTION

The present invention accelerates grains from an impeller by centrifugal force outwardly toward a wall surrounding the impeller so that the grains reach the wall at a reasonably consistent velocity. By smashing the grains into the impact wall at standard speeds and under controlled conditions, the amount of breakage obtained in a relatively small sample of the grain can be used to reliably distinguish between those batches of grain which will experience more breakage and those batches which will experience less breakage during shipment. The tester operates in an automatic manner, with very little attention required by the operator, and can process a sample large enough to provide a reliable prediction in a very short period of time.

The tester meters grains downwardly from a funnel shaped hopper one at a time through a tube into the center of a disk shaped rotating impeller. The impeller disk has channels formed in the top surface which extend out radially from the center of the disk to the rim of the disk. The top of the disk is preferably covered by a plate which also forms a cover over the channels to prevent the grains from flying upwardly out of the impeller. The tube which guides the grains extends downwardly through an opening in the center of the plate at the top of the impeller such that the grains hit the spinning disk near its center, migrate outwardly toward the channels, engage the walls of one of the channels, and rapidly accelerate outwardly until they leave the spinning disk. The housing of the tester includes a smooth, cylindrical inner impact wall which surrounds the impeller and is spaced away from the rim of the impeller a distance which is close enough that the discharged grains do not substantially lose speed before hitting the wall but far enough away that the grains will not bounce back from the impact wall and hit the impeller. After hitting the wall, the grains drop downwardly into a sample collection chute which funnels the grains down to a sample collection box. The tested sample is then manually screened and the percentage of broken grains calculated.

The structure of the impeller, comprising a solid disk with channels formed therein, provides minimal agitation of the air around the impeller and between the impeller and the impact wall. The air agitation that does take place is primarily directed radially outward from the channels; the impeller acts, in effect, as a rotary vane pump, drawing air in through the center of the impeller and blowing it out through the exit ports of the channels in the rim of the impeller disk. The relatively constant, outwardly directed air flow from the impeller causes the grains to move in consistent, horizontal paths to the impact cylinder wall so that all the grains will hit the wall at similar angles (to a plane tangent to the wall at the point of impact).

The impeller is mounted on a rotating vertical shaft driven by a motor controlled to maintain a substantially constant speed. The metering apparatus which delivers the seeds one at a time from the hopper into the impeller is also driven at a controlled speed to insure that the grains enter the impeller individually and do not interfere with one another as they are being ejected into the impact chamber.

Further objects, features and advantages of the invention will be apparent from the following detailed description taken in conjunction with the accompanying drawings showing a preferred embodiment of an apparatus for testing grains for resistance to damage.

BEST MODE FOR CARRYING OUT THE INVENTION

Figure 1:
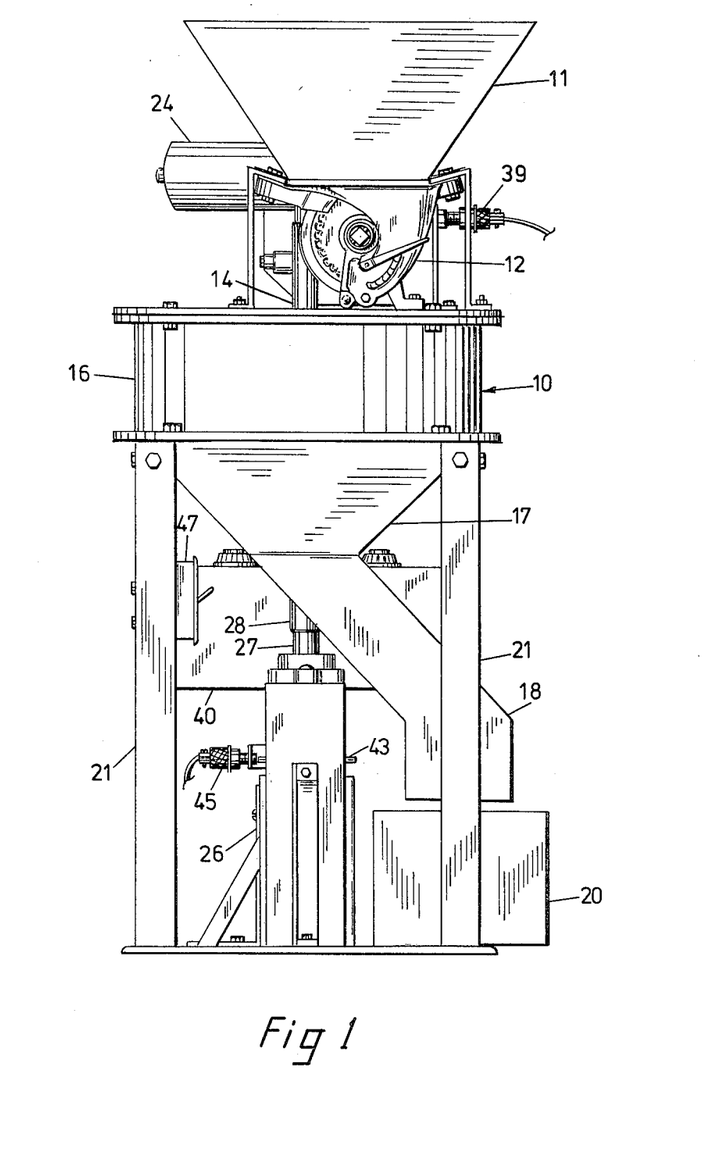
FIG. 1 is a front elevation view of an apparatus for testing grain for resistance to damage in accordance with the invention.

With particular reference to the drawings, a preferred embodiment of an apparatus for testing grain for resistance to damage is shown generally at 10 in FIG. 1. The apparatus 10 includes a hopper 11 for holding a sample of grain to be tested and a metering section 12 for receiving the grain from the hopper 11 and metering it one kernel at a time downwardly through an infeed tube 14. The incoming grains are received within an impact housing 16 from whence the discharged grains pass to a collection chute 17 which delivers the grain through a closed guide channel 18 to a sample collection box 20. These components are supported on a frame 21 preferably composed of steel angle members.

Figure 2:
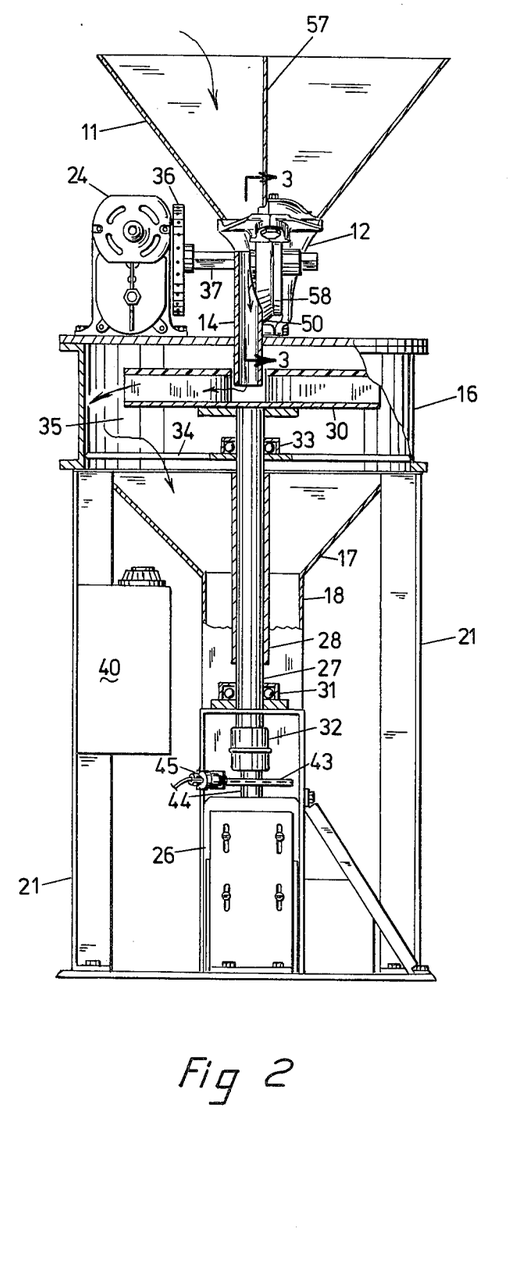
FIG. 2 is a side elevation view of the apparatus taken from the left side of FIG. 1, with portions of the apparatus broken away to show the internal parts.

The grain metering unit 12 is driven by a fractional horsepower electric gear motor 24. A universal motor 26 is mounted in an upright position at the bottom of the frame 21 and has its output shaft coupled to a vertical drive shaft 27 which extends through a tight fitting sleeve 28 up into the collection chute 17. As best shown in the view of FIG. 2, in which portions of the walls of the device have been broken away to illustrate the interior components, the shaft 27 extends up into the chamber defined within the impact housing 16 and is attached at its top end to the center of a disk shaped impeller 30. The shaft 27 is mounted for rotation in a vertical axis by a lower bearing 31, mounted just above the position of the coupling 32 between the end of the shaft of the motor 26 and the bottom of the shaft 27, and an upper bearing 33 which is attached to metal cross members 34 which extend across the bottom of the cylindrical impact chamber defined by the inner impact wall 35. The upper bearing 33 is particularly important since it provides a firm support for the upper end of the shaft 27 just below the point of attachment between the shaft and the impeller 30. This bearing, which is preferably sealed to prevent contamination by fine dust particles, stabilizes the rotation of the shaft and impeller to minimize vibration of the structures at high rotational speeds.

It is very desirable that the inner surface 35 of the impact housing 16 be smooth and hard, preferably being made of polished steel, to minimize any variations in the impact forces experienced by the grains.

To monitor the input feed rate of the metering unit 12, a magnetic pick-up actuating disk 36 is mounted to the shaft 37 which extends from the gear motor 24 to the metering unit 12, and a magnetic pick-up head 39 is mounted adjacent to the disk 36 in position to detect the changes in the magnetic field as the disk rotates and therefore provide pulses to a frequency counter (not shown) within a control panel 40 to display the rate of rotation of the gear motor. Similarly, a magnetic pick-up actuating disk 43 is mounted to the shaft 44 extending from the motor 26, and a pick-up head 45 is mounted adjacent to the disk 43. Again, the head 45 transmits electrical pulses to the control panel 40 at a rate which is proportional to the rate of rotation of the shaft 44. The control panel 40 may include a standard SCR motor control unit adapted to vary the rate of speed of the motors 26 and 24, or a manual autotransformer may be utilized. An automatic feedback control system can also be utilized, if desired, to regulate the rate of speed of the motor 26 automatically to compensate for variations in the impeller speed caused by transient conditions. Such motor controllers are well known and commercially available. A switch 47 is provided to switch either the output of the pick-up head 39 or 45 to the frequency control at the control panel. Generally, the speed of the drive motor 26 requires regular monitoring, while the speed of the motor 24 is less critical.

Figure 3:
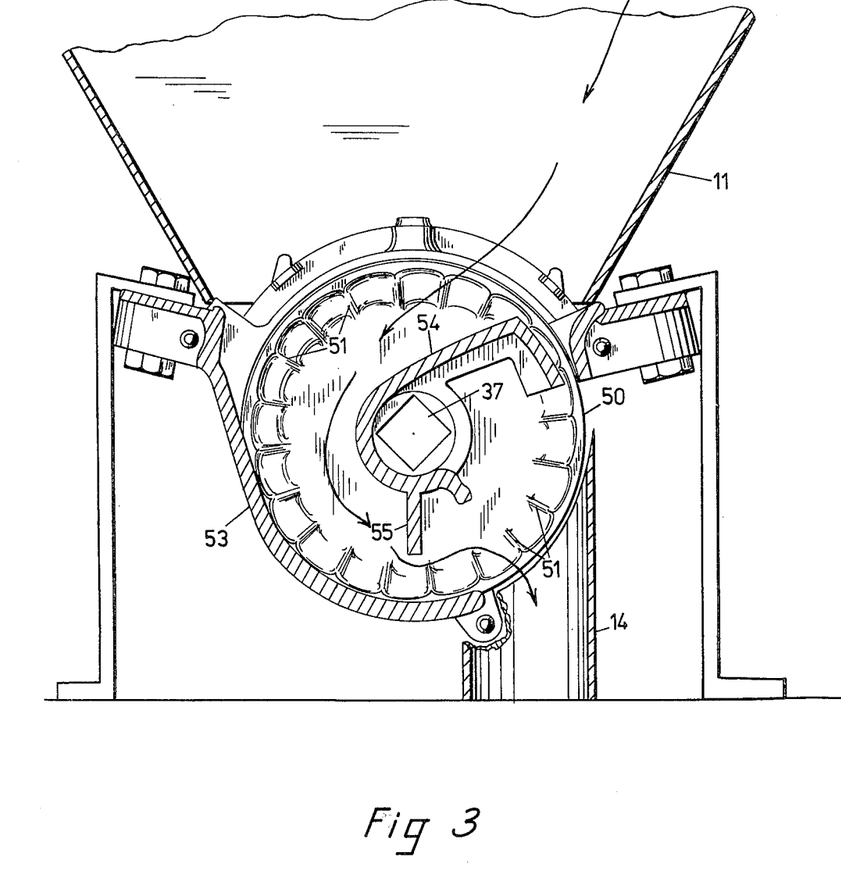
FIG. 3 is a cross sectional view of the metering portion of the apparatus taken generally along the lines 3—3 of FIG. 2.

A cross section of the metering unit 12 is shown in the view of FIG. 3. As illustrated therein, the metering device, similar to a standard grain drill, utilizes a cup shaped wheel 50, mounted to the shaft 37, which has flutes 51 along its rim which define indentations generally conforming to the expected size of the individual grains to be dispensed. The wheel 50 rotates on the shaft 37 within a housing 53 which is mounted directly below the hopper 11. As the wheel 50 rotates in a counterclockwise direction, it draws grain along with it from the hopper and causes a line of grains to form along the perimeter of the wheel generally fitting within the depressions defined within the flutes 51. A flange 54 extends across the top of the wheel, then downwardly and around the shaft 37, and has a downwardly depending finger 55 which terminates at a position just above the bottom of the housing 53 at a distance therefrom approximately equal to the expected height of one kernel of grain. Thus, one grain at a time will be carried under the depending finger 55 and dropped out into the tube 14. It may be noted that the hopper 11 is divided by a central plate 57 into two portions, with the left hand portion shown in FIG. 2 feeding down into the wheel portion of the metering device 12 which is shown in FIG. 3. The other side of the hopper 11, which is shown closed off in FIG. 2, may be used when feeding grains of another size into the tester since the side of the metering device opposite to the wheel 50 includes another wheel 58 which has, for example, smaller and shorter undulations therein to accommodate smaller grains. Where the outer side of the hopper is used, the tube 14 may be replaced with a tube which is shaped to receive grains discharged from the wheel 58.

Figure 4:
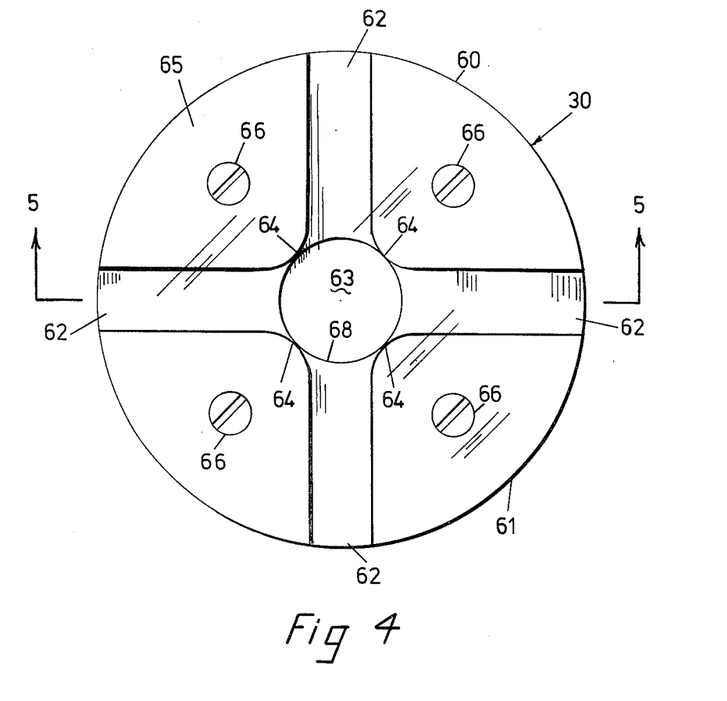
FIG. 4 is a top plan view of the impeller portion of the apparatus.
Figure 5:
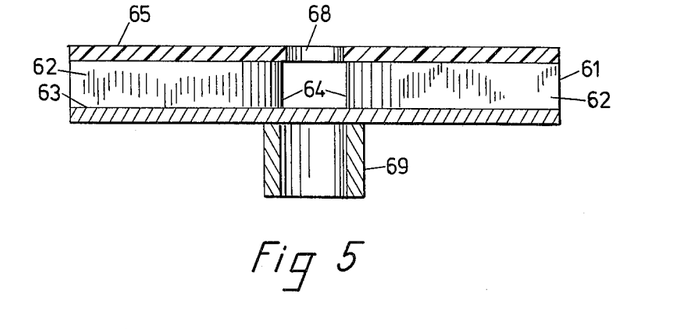
FIG. 5 is a cross sectional view of the impeller of FIG. 4 taken generally along the lines 5—5 of FIG. 4.

The structure of the impeller 30 is best shown with reference to the views of FIGS. 4 and 5. The impeller consists of a circular disk body 60, preferably made of aluminum, which has a substantial thickness, and which terminates in an upright peripheral rim 61. Four radially extending channels 62 are formed in the top face of the disk body 60 and bottom out on a flat bottom surface 63. The channels have smooth side walls which intersect with one another at curved corners 64 which are spaced around a central portion of the disk where the channels intersect. A circular cover plate 65 is mounted to the top surface of the disk 60 body by screws 66 and covers each of the four channels 62 except at the central portion of the disk where a circular opening 68 is formed in the cover. The cover may be formed of clear plastic, as shown to allow a view inside the impeller, or of other materials such as aluminum.

As shown in FIG. 5, a short metal sleeve 69 is attached to the bottom center of the disk body and has an inner bore which is adapted to tightly receive and hold the top end of the drive shaft 27. A set screw (not shown) or other attachment fastener may be used to hold the impeller in place on the shaft.

The impeller construction shown provides a highly efficient, extremely reliable accelerator for the grains which are to be tested. The individual grains that pass through the metering device 12 and through the tube 14 strike the very center of the impeller and gravitate over to one of the side walls of the channels 62. As shown in FIG. 2, the tube 14 preferably extends downwardly below the top of the cover 65, with the outer periphery of the tube 14 being spaced just inside the walls of the opening 68, so as to minimize the possibility that a grain dropped into the center of the impeller will bounce back out again. The grains so deposited will migrate toward the side walls of the channels 62 and, when engaging these walls, will slide outwardly along them and be rapidly accelerated to a very high rate of speed which is dependent upon the speed of rotation of the impeller and its diameter, as well as upon variable characteristics of the grain, such as moisture content, weight, and coefficient of friction. It has been found that with an impeller having a 254 mm (10 inches) diameter, mounted within an impact cylinder 16 having an inner diameter of 304.8 mm (12 inches), satisfactory discrimination of the breakage tendency of various grains of corn can be obtained with an impeller speed of 2400 r.p.m. This leaves about 25.4 mm (1 inch) clearance between the rim 61 of the impeller and the inner cylindrical wall 35. Adequate disk performance has been obtained with a disk body 60 having a thickness of 25 mm and channels 62 being formed 20 mm deep and 25 mm wide. The curved side walls 64 are, with the foregoing dimensions for the channels, preferably formed with a 60 mm radius, although satisfactory results may also be obtained if the sharp corner at the intersection between walls of the intersecting channels is simply ground off flat.

The relative thickness of the disk body 60 gives the impeller substantial rotational inertia so that the speed of the disk does not substantially change as seeds are deposited for acceleration. Moreover, the design of the impeller minimizes air turbulence at the rim which, if excessive, could deflect the path of the seeds ejected from the impeller in random manners, thereby degrading the repeatability and reliability of the test. This is a serious problem with previous rotational impeller designs which utilize vanes or tubes, both of which generate random air currents surrounding the impeller which disturb the path of motion of the seeds in unpredictable ways. The impeller 30 is substantially a solid cylinder, since the tops of the channels 62 are closed off by the cover plate 65, and the rim 61 of the impeller is a smooth cylindrical surface except for the openings at which the channels 62 exit. Since these channels are relatively narrow compared to the overall diameter of the disk body, the air surrounding the rim of the disk is not substantially agitated. However, it may be observed that the rotating disk does not act to draw air in through its top opening 68, primarily from the input tube 14, and to discharge this air through the rim openings of each of the channels 62. This air is directed radially outwardly at the point of exit, and thus aids, rather than interferes with, the desired straight, horizontal path of motion of the seeds discharged from the impeller. Moreover, the outwardly directed air, which must be forced downwardly in the impact chamber since the top of the chamber is closed, helps to carry the seeds downwardly after they have hit the wall of the impact cylinder, and thus away from the rotating impeller. As noted above, it is desirable that these seeds not move back toward the impeller since otherwise they might rebound into the channels and interfere with the ejection of following seeds.

Although four radial channels have been shown formed in the disk body, a preferred embodiment, a single channel—equivalent to two aligned radial channels of one radius length—could also be utilized.

The apparatus of the invention is especially adapted for testing corn samples to determine the susceptibility of the corn to breakage during handling. For greatest reliability in the testing, the corn samples are first allowed to reach room temperature, and the relative humidity at the time of the test is measured and the moisture content of the samples determined using the air oven method. To prepare the corn for breakage testing, each sample may be sieved using a 12/64 inch round hole sieve, with the broken particles and smaller foreign material passing through the sieve and the larger size foreign materials which are retained on the sieve being removed by hand. The whole kernels retained on the sieve may then be poured into the hopper 11 of the tester 10. The impacted corn collected in the box 20 is then screened over the 12/64 inch round hole sieve. All the kernels remaining on the sieve, even if broken or cracked, are regarded as whole grains. The material retained on the sieve can then be weighed and its weight compared to the weight of the original sample to compute the percent beakage. A small sample can be processed through the testing apparatus in this manner in about ten to fifteen seconds. Tests performed on multiple samples taken from the same batch of corn show very small standard deviations of the percent breakage, generally averaging less than one percent, thereby confirming the reliability of the testing procedure and demonstrating a capability of distinguishing between batches of corn that are close but not identical in their susceptibility to breakage.

It is understood that the invention is not confined to the particular construction and arrangement of parts herein illustrated and described, but embraces such modified forms thereof as come within the scope of the following claims.

What is claimed is:

1. Apparatus for testing agricultural grains for resistance to damage, comprising:
   (a) a housing having a smooth, cylindrical inner impact wall;
   (b) an impeller mounted for rotation within the housing having a cylindrical disk body with two opposite faces and a cylindrical peripheral rim, radial channels formed in one of the faces extending most of the distance of the radius of the disk body and intersecting at the center of the disk body and adapted to receive grains for testing at such center, the channels being narrow relative to the diameter of the disk body, and;
   (c) means for rotating the impeller at a substantially constant rotational speed.

2. The apparatus of claim 1 including a cover mounted to the one face of the disk body to cover the channels and having a central opening to allow grains to pass therethrough to fall at the center of the disk body at the intersection of the bottom of the channels.

3. The apparatus of claim 2 including means for metering grains one at a time through the central opening in the cover on the impeller into the center of the impeller body at the intersection of the channels therein.

4. The apparatus of claim 1 wherein the impeller is mounted for rotation on a vertical shaft attached to the bottom center of the impeller disk body, the shaft extending downwardly and being held for rotation by at least two bearings spaced vertically apart, and wherein the means for rotating the impeller includes a controlled speed electric motor coupled to the vertical shaft.

5. The apparatus of claim 1 including a collection chute mounted beneath the impeller and attached to the impact housing and extending downwardly to collect the grains discharged from the impeller and direct them to a collection box located below the discharge end of the colection chute.

6. The apparatus of claim 5 including a magnetic pick-up actuating disk mounted to the vertical shaft and an electrical pick-up mounted adjacent thereto and adapted to detect the motion of the magnetic actuating disk and thereby monitor the speed of rotation of the vertical shaft.

7. The apparatus of claim 2 wherein the impeller is approximately 10 inches in diameter and 1 inch thick, and the inner impact wall is approximately 12 inches in diameter, and wherein the channels formed in the impeller are approximately 1 inch wide, and the cover on the impeller is formed of a solid circular plate having a central circular opening.

8. The apparatus of claim 1 or 2 wherein there are four radially directed channels in the disk body and the corners at the intersection of the walls defining the channels in the disk body are rounded to minimize random damage to the grains when they are dropped into the impeller.

9. Apparatus for testing agricultural grains for resistance to damage, comprising:
   (a) a housing having a smooth, cylindrical inner impact wall;
   (b) an impeller within the housing having a cylindrical disk body with two opposite faces and a cylindrical peripheral rim, not more than four radial channels formed in one of the faces which are narrow relative to the diameter of the disk body and which intersect at the center of the disk body, and a cover mounted to the one face over the channels and having a central opening to allow grains to pass therethrough to fall on the center of the disk body at the intersection of the bottom of the channels;
   (c) a vertical shaft attached to the bottom center of the impeller disk body to mount the impeller for rotation, the shaft extending downwardly and being held for rotation;
   (d) means for metering grains one at a time through the center opening in the cover on the impeller into the center of the impeller body at the intersection of the channels therein; and
   (e) means for rotating the vertical shaft, and thereby the impeller, at a substantially constant rotational speed.

10. The apparatus of claim 10 including a collection chute mounted beneath the impeller and attached to the impact housing and extending downwardly to collect the grains discharged from the impeller and direct them to a collection box located below the discharge end of the collection chute.

11. The apparatus of claim 10 including a magnetic pick-up actuating disk mounted to the vertical shaft and an electrical pick-up mounted adjacent thereto and adapted to detect the motion of the magnetic actuating disk and thereby monitor the speed of rotation of the vertical shaft.

12. The apparatus of claim 10 wherein the impeller is approximately 10 inches in diameter and 1 inch thick, and the inner impact wall is approximately 12 inches in diameter, and wherein the channels formed in the impeller are approximately 1 inch wide, and the cover on the impeller is formed of a solid circular plate having a central circular opening.

13. The apparatus of claim 10 wherein there are four radially directed channels in the disk body and the corners at the intersection of the walls defining the channels in the disk body are rounded to minimize random damage to the grains when they are dropped into the impeller.

14. Apparatus for testing agricultural grains for resistance to damage, comprising:
   (a) a housing having a smooth, cylindrical inner impact wall;
   (b) an impeller mounted for rotation within the housing having a cylindrical disk body with two opposite faces and a peripheral rim, radial channels formed in one of the faces and intersecting at the center of the disk body and adapted to receive grains for testing at such center, a cover mounted to one face of the disk body to cover the channels and having a central opening to allow grains to pass therethrough to fall at the center of the disk body at the intersection of the bottom of the channels;
   (c) means for rotating the impeller at a substantially constant rotational speed; and
   (d) means for metering grains one at a time through the central opening in the cover on the impeller into the center of the impeller body at the intersection of the channels therein including a circular wheel having flutes formed therein along the peripheral edge with the undulations of the flutes being approximately the size of the grains to be tested, a hopper for holding a sample of grains and discharging them into engagement with the fluted wheel, a constant speed drive motor connected to the fluted wheel to rotate it in a vertical plane below the hopper at a substantially constant speed, a housing surrounding the fluted wheel to guide and hold the grains and including a depending finger cooperating with the flutes on the wheel so that the grains pass therethrough at the bottom of the fluted wheel one grain at a time, a tube extending downwardly from the bottom of the fluted wheel and positioned to receive grains discharged from the fluted wheel and direct them through the central opening in the cover of the impeller, with the bottom end of the tube being spaced above the center of the disk where the channels therein intersect.

* * * * *

UNITED STATES PATENT AND TRADEMARK OFFICE
CERTIFICATE OF CORRECTION

PATENT NO. : 4,422,319
DATED : December 27, 1983
INVENTOR(S) : Marshall F. Finner, Shiw S. Singh It is certified that error appears in the above–identified patent and that said Letters Patent are hereby corrected as shown below:

Col. 6, line 17, omit "not".

Col. 7, line 42, "Claim 5" should read --Claim 4--.

Col. 8, line 19, "Claim 10" should read --Claim 9--.

Col. 8, line 25, "Claim 10" should read --Claim 9--.

Col. 8, line 31, "Claim 10" should read --Claim 9--.

Col. 8, line 38, "Claim 10" should read --Claim 9--.

Signed and Sealed this

First Day of May 1984

[SEAL]

Attest:

GERALD J. MOSSINGHOFF

*Attesting Officer*  *Commissioner of Patents and Trademarks*